Dec. 17, 1940. J. T. GURALY, JR Plant Pat. 435
PEAR TREE
Filed Oct. 10, 1939
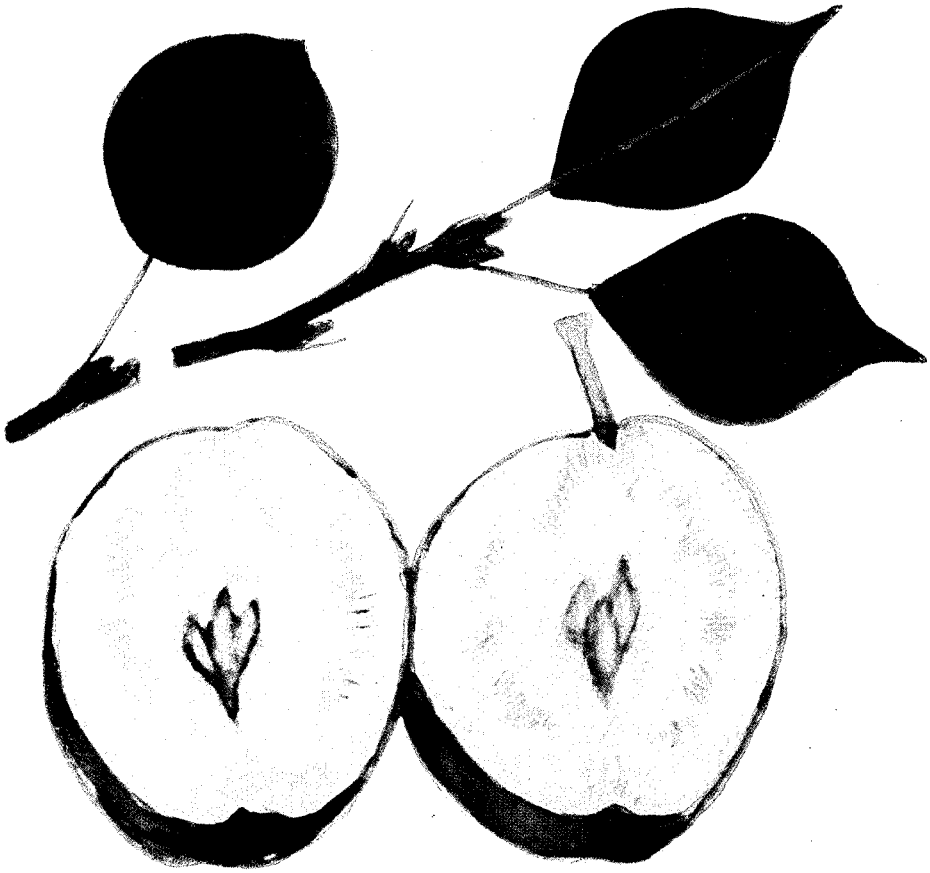
INVENTOR.
JOSEPH T. GURALY, JR.
BY Richey & Watts
ATTORNEY.

Patented Dec. 17, 1940

Plant Pat. 435

UNITED STATES PATENT OFFICE

435

PEAR TREE

Joseph T. Guraly, Jr., Fairport Harbor, Ohio

Application October 10, 1939, Serial No. 298,816

1 Claim. (Cl. 47—62)

This invention relates to a new and distinct variety of pear tree which is asexually produced from a seedling variation and which is characterized by heavy foliage having an unusual shaped leaf, early bearing and early ripening fruit, which fruit is of unusual shape and has colored flesh.

This new pear was discovered incident to sowing of a group of seeds of unknown origin. Among the plants grown from these seeds was one which had small fruit, but which fruit was unusual due to the peculiar coloring of the flesh of the fruit, as well as being a fruit which ripened much earlier than other types.

Buds from this tree were budded to a pear tree of the Clapp variety. Due to a blight disease, further buds from the budded portions of the Clapp tree were budded onto a Duchess Dwarf pear tree. A bud from the Duchess was then grafted onto a seedling. The result was a pear tree having fruit colored as in the original seedling, but distinctly larger and different in shape than those of the original seedling. This tree is now growing and bearing fruit in its second season at 637 Plum Street, Fairport Harbor, Ohio. It bore three pears the first year and about eighteen pears the second year.

The new variety is valuable because it ripens during a period before other pears are normally ripened, namely, about August 1st, and it is further valuable because the fruit is of a different shape and shows a striking interior coloring not known to other pears.

The following is a brief description, and is illustrated by the accompanying drawing which shows a portion of the tree foliage illustrating the shape of the leaves on different portions of a branch; a specimen of the fruit is also shown, being split open to show the striking red color of the flesh.

The tree has a tendency to grow tall rather than spread out. The foliage is a dark green and the leaves, instead of having the usual long narrow leaf common to the ordinary pear trees, are relatively wide and short. In the individual branches, the leaves at the base are wide and short, being almost circular with a substantially round end. The leaves toward the end of the branches, however, while retaining the body characteristics, have a sharp point extending from the end of the body of the leaf.

The fruit of the tree, which ripens early in August, is particularly characterized by its lack of the usual pear shape. That is, it has a generally round uniform shape which is more like that of a quince without the usual elongated part near the stem common to most varieties of pears. The color of the exterior is generally a brownish green. The side away from the sun is usually lacking in the brownish cast and has a plurality of small fine yellow dots. The inside of the fruit has a coarse grained flesh and usually is a bright red with yellow and white veins. The flesh is sweet, juicy, having a rich pear flavor. The illustration shows one of the pears in which the coloring was somewhat more subdued than the majority of the fruit.

Tree:
- Medium.
- Vigorous.
- Upright.
- Tall, medium dense.
- Rapid growing.
- Hardy, very productive.
- Regular bearer.

*Trunk:*
- Medium, smooth.

*Branches:*
- Medium, smooth.
- Straight, reddish brown.

*Lenticels:*
- Medium in number and size.

*Leaves:*
- 2½" long and 1¾" wide.
- Short, ovate.
- Abruptly pointed; sometimes hardly any point.
- Medium thick.
- Very dark green, smooth.

*Margin:*
- Finely serrate.

*Petiole:*
- 1" long, medium long and thick.

*Flowers:*
- Bloom on May 5th, same time as Bartlett, early, large.
- Pink white.
- Fertile, semi-double 5 to 9 petals.

Fruit:
- August 15th to 20th—2 week season.
- Hangs very well.
- Large size fruit.
- Uniform.
- Regular roundish.
- Ovate.
- Unsymmetrical sides—unequal.
- Uniform.
- Medium stem.

*Stem:*
- Medium—about 1" long.

*Cavity:*
- Shallow.
- Obtuse.
- Smooth—symmetrical.

*Calyx:*
- Partly open.
- Medium size.

*Lobes:*
Connivent, medium.
*Basin:*
Smooth.
Shallow.
*Skin:*
Thick.
Smooth.
Waxen glossy.
*Color:*
Reddish brown—intermixed with green.
*Flesh:*
White with strong bright red streaks very close together extending radially from the core.
Coarse.
Crisp, juicy, sweet, with strong pear flavor.
*Quality:*
Very good.
*Core:*
Small, closed, axial.
Core lines meeting.
*Calyx-tube:*
Long, narrow.
*Seed:*
Long, large, plump.
*Use:*
Dessert, kitchen, market, home.

Good keeping qualities and striking color make it especially desirable for decorative purposes, etc.

I claim:

A new and distinct variety of pear tree substantially as shown and described characterized by the shape of the leaves of its foliage, and by the roundness of shape of its fruit, and by the generally red coloring of the flesh of the fruit and the yellow and white veins and the early ripening of the fruit.

JOSEPH T. GURALY, Jr.